(12) United States Patent
McPhail et al.

(10) Patent No.: US 9,256,081 B2
(45) Date of Patent: Feb. 9, 2016

(54) PROTECTIVE EYEWEAR (71) Applicant: Warrior Sports, Inc., Warren, MI (US)

(72) Inventors: Matthew W. McPhail, Royal Oak, MI (US); Richard J. Janisse, Windsor (CA)

(73) Assignee: Warrior Sports, Inc., Warren, MI (US)

( * ) Notice: Subject to any disclaimer, the term of this patent is extended or adjusted under 35 U.S.C. 154(b) by 39 days.

(21) Appl. No.: 14/467,662

(22) Filed: Aug. 25, 2014

(65) Prior Publication Data

US 2015/0103307 A1 Apr. 16, 2015

Related U.S. Application Data (60) Provisional application No. 61/889,611, filed on Oct. 11, 2013.

(51) Int. Cl.
G02C 3/00 (2006.01)
A61F 9/02 (2006.01)
G02C 5/00 (2006.01)

(52) U.S. Cl.
CPC ............. *G02C 5/001* (2013.01); *A61F 9/027* (2013.01); *G02C 3/003* (2013.01)

(58) Field of Classification Search
CPC .......... G02C 3/003; G02C 3/006; A61F 9/02; A61F 9/027
USPC .......... 351/156, 157, 158, 44, 41; 2/452, 448, 2/426
See application file for complete search history.

(56) References Cited

U.S. PATENT DOCUMENTS

| | | |
|---|---|---|
| 5,303,428 A | 4/1994 | Pernicka |
| 5,321,443 A | 6/1994 | Huber et al. |
| 5,406,340 A * | 4/1995 | Hoff .................. A61F 9/027 2/452 |
| 5,408,702 A | 4/1995 | Chiang |
| 5,410,763 A | 5/1995 | Bolle |
| 5,566,427 A | 10/1996 | Lathrop |
| 5,802,622 A | 9/1998 | Baharad et al. |
| 6,276,795 B1 | 8/2001 | Hall et al. |
| 6,321,391 B1 | 11/2001 | Basso |
| 6,511,177 B1 | 1/2003 | Hall et al. |
| 6,704,944 B2 | 3/2004 | Kawainshi et al. |
| 7,000,263 B2 | 2/2006 | McNeal |
| 7,003,811 B2 | 2/2006 | Canavan |
| 7,162,750 B2 | 1/2007 | Canavan |
| 7,181,779 B2 | 2/2007 | Hussey |
| 7,222,370 B2 | 5/2007 | Gait |
| 7,260,854 B2 | 8/2007 | Hahn et al. |
| 7,617,544 B2 | 11/2009 | Hahn et al. |
| 7,992,228 B2 | 8/2011 | Milea et al. |
| 8,011,026 B2 | 9/2011 | Stevens |
| 8,316,470 B2 | 11/2012 | McNeal et al. |
| 8,327,466 B2 | 12/2012 | Hahn et al. |
| 8,782,821 B2 | 7/2014 | Brown |
| 2008/0295299 A1 | 12/2008 | Christian |
| 2009/0038059 A1 | 2/2009 | McNeal et al. |
| 2011/0267575 A1 | 11/2011 | Batey |
| 2012/0233734 A1 | 9/2012 | Lebel et al. |

\* cited by examiner

*Primary Examiner* — Hung Dang
(74) *Attorney, Agent, or Firm* — Warner Norcross & Judd LLP (57) ABSTRACT

Protective eyewear includes a frame having a first side with a first member and an opposing second side with a second member. A foldable strap has openings at either end and is folded about the first and/or the second member and is held in place by a clip. The clip has a base portion and a swivel portion. The base portion and the swivel portion of the clip engage one another at least partially within the openings of the folded strap. The swivel portion has a range of rotation relative to the base portion of the clip.

20 Claims, 5 Drawing Sheets

PROTECTIVE EYEWEAR

BACKGROUND OF THE INVENTION

The present invention relates generally to protective sports equipment, and more particularly to protective eyewear for use during sports such as lacrosse and field hockey.

Lacrosse and field hockey are rough contact sports, and injuries to players are not uncommon. Such injuries can be caused by bodily contact with another player or by being struck with a stick. Contact with a lacrosse ball also can cause injuries because lacrosse balls are relatively heavy and travel at high speeds during play. As a result, players use a variety of protective equipment to avoid these injuries. For example, players typically use protective gloves, arm pads, shoulder pads, helmets and face guards.

Some types of protective equipment have been adapted specifically for male and female players. For example, male players often use helmets with face guards, while female players typically use a smaller protective eyewear device, such as goggles. Goggles, however, are typically formed from a polycarbonate material or a steel cage and can produce glare in the sun. They can also fog up, particularly in cold, wet or humid weather. Further, caged or bulky goggles can impede a player's vision and can be easily scratched or shattered.

Conventional goggles typically include an elastic strap that extends around the player's head to secure the goggles over the player's eyes. Such a strap is impractical for female players, who typically tie their hair back, for example, in a ponytail. A female player can position the strap above her ponytail, but the strap will likely pull the goggles upward on her face. Additionally, positioning the strap too high on the player's head can result in the elastic force of the strap sliding the strap over the player's head, which may cause the goggles to fall off. Alternatively, the player can locate the strap below her ponytail, which can pull the goggles downward on the player's face and ears.

SUMMARY OF THE INVENTION

Protective eyewear is provided that is comfortable for players and that reliably maintains its position on a player's face and head.

In one embodiment, there is provided a protective eyewear system including: a frame with a first side having a first member and an opposing, second side having a second member. A folded strap, with openings at each of two opposing ends, is folded about the first and/or second member with the openings at each end substantially aligned in the folded configuration.

In another embodiment, the system includes a clip having a base portion and a swivel portion that engage one another at least partially within the openings of the folded strap. The swivel portion has a range of rotation relative to a base portion. A head strap is attached to the swivel portion of the clip and is moveable within a range of rotation of the swivel portion.

In yet another embodiment, the frame includes a lower member extending substantially below the first and second members as viewed when the eyewear system is worn. An upper member of the frame extends substantially above the first and second members as viewed when the eyewear system is worn.

The protective eyewear of the current embodiments is easily adjusted, comfortable to wear, and consistently locates upon a wearer's head. With the folded strap, the frame can be resiliently pulled toward the user's face and adjusted in position without discomfort.

These and other objects, advantages, and features of the invention will be more fully understood and appreciated by reference to the description of the current embodiment and the drawings.

Before the embodiments herein are explained in detail, it is to be understood that the invention is not limited to the details of operation or to the details of construction and the arrangement of the components set forth in the following description or illustrated in the drawings. The invention can be implemented in various other embodiments and of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration can be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components.

DETAILED DESCRIPTION OF THE CURRENT EMBODIMENTS

Protective eyewear in accordance with a current embodiment is shown in FIGS. 1-4 and is generally designated 10. The protective eyewear 10 includes a frame 12 having a first end 14 and an opposing second end 16. Eye protector members 18, 19, 21 can be joined with the frame 12, and may extend laterally across the face of a wearer W.

In particular, the foldable strap 20 can be folded around at least one of the first and second ends 14, 16 of the frame 12. The frame 12 can be connected to a head strap 50 by engagement of a clip 30 with both the foldable strap 20 and head strap 50. Given that the protective eyewear 10 can include the foldable strap 20 and clip 30 adapted to connect the head strap 50 to the frame 12 identically or substantially similarly on both sides 14, 16, only one foldable strap 20 and clip 30 will be described in detail herein.

Figure 6:
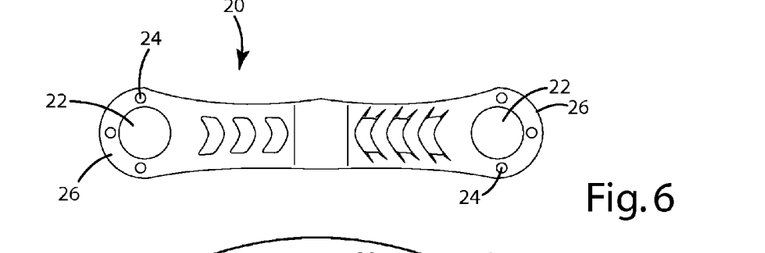
FIG. 6 is a front view of a foldable strap in an extended mode.

As shown in FIG. 6, the folded strap 20 can include an opening 22 at each end 26 that are substantially aligned when folded around the first and/or second ends 14, 16 of the frame 12. The openings 22 can be identical in size and/or shape, or may differ in size and/or shape. If the size and/or shape of the openings 22 differ on opposite ends 26, at least a portion of the openings can align, creating a passage through the aligned openings 22 to receive at least a portion a clip 30. The ends 26 of the foldable strap 20 can be held together by the clip 30.

Figure 7:
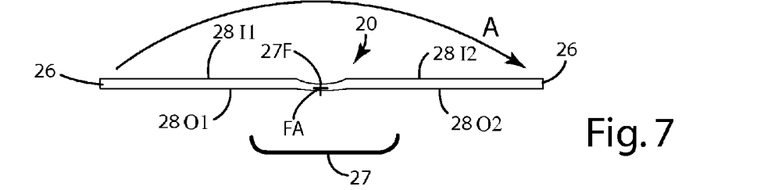
FIG. 7 is a top view of the foldable strap in an extended mode.

The strap can include a foldable portion 27, which as shown in FIG. 7, can be near the center of the strap. Of course, the foldable portion 27 can be elsewhere along the strap, for example, nearer one of the two ends. This foldable portion can optionally include a folding feature 27F which can be in the form of a reduced cross section, perforations, a recess, different or softer material, or some other component having increased flexibility or weakness as compared to the remainder of the strap. Of course, the strap can include no folding feature, and can be simply folded over upon itself in any desired location, but optionally near the center of the strap. As also shown in FIG. 7, the strap can include a first inner surface 28I1 and a second inner surface 28I2, and first and second outer surfaces 28O1 and 28O2 opposite the respective inner surfaces. The strap can fold about a fold axis FA in the direction of arrow A, so that the first and second inner surfaces 28I1 and 28I2 come into contact with and engage one another. When the clip 30 is joined with the strap, these surfaces can be locked into engagement with one another. Optionally, any first or second member 14L, 16L, that is disposed between the opposing ends of the strap, or between the inner surfaces, or adjacent the folding feature or folding axis, can be trapped or secured between the folded over parts of the strap, particularly when the clip 30 is installed.

Figure 8:
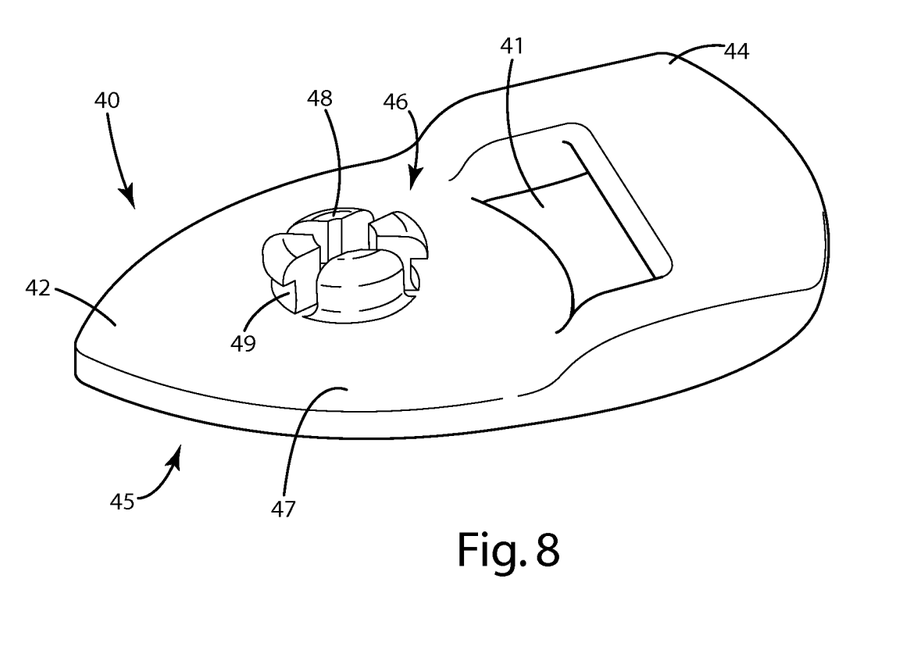
FIG. 8 is a perspective view of a swivel tab of a clip.
Figure 9:
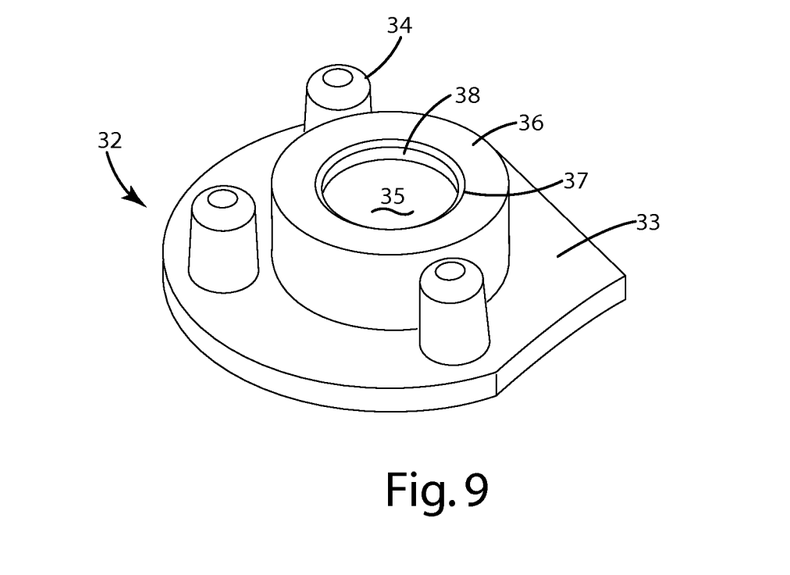
FIG. 9 is a perspective view of a base of the clip.

The clip 30 can include a base 32 as shown in FIG. 9 and a swivel portion or tab 40 as shown in FIG. 8. The base 32 of the clip 30 can include protrusions 34 that align with apertures 24 defined by the foldable strap 20. These protrusions can be fixed on the base 32 by molding or with suitable fasteners, or can be integrally formed with the base 32 during manufacture. In the illustrated embodiment, three apertures 24 are positioned to partially surround the openings 22 in the foldable strap 20, but can be positioned anywhere on the foldable strap 20.

When the strap 20 is folded, the apertures 24 on each end 26 may substantially align with the apertures 24 on the opposite end 26 of the foldable strap 20. The protrusions 34 of the base 32 may align with and fit into the apertures 24 in the foldable strap 20. Once in position, the base 32 of the clip 30 can be fixed in position and non-rotatable relative to the foldable strap 20. While the illustrated embodiment is shown having protrusions 34 on the base portion of the clip 30 and the apertures 24 on the foldable strap 20, it should be understood that the protrusions can be included on the strap 20 and the apertures 24 on the base 32 of the strap 20. Further, it should be understood that the apertures 24 can be indentations rather than apertures, and any number of the protrusions, indentations or apertures can be used.

As shown in FIG. 9, the base 32 of the clip 30 may further include a raised ring 36 with a rail 38 on at least part of the circumference of the raised ring 36. The rail 38 may extend from a distal end 37 of the raised ring 36 toward the center of the ring 36. The swivel tab 40 of the clip 30 can include a foldable strap portion 42 that engages the base 32 of the clip 30 and a head strap portion 44 to which the head strap 50 can be affixed.

Figure 11:
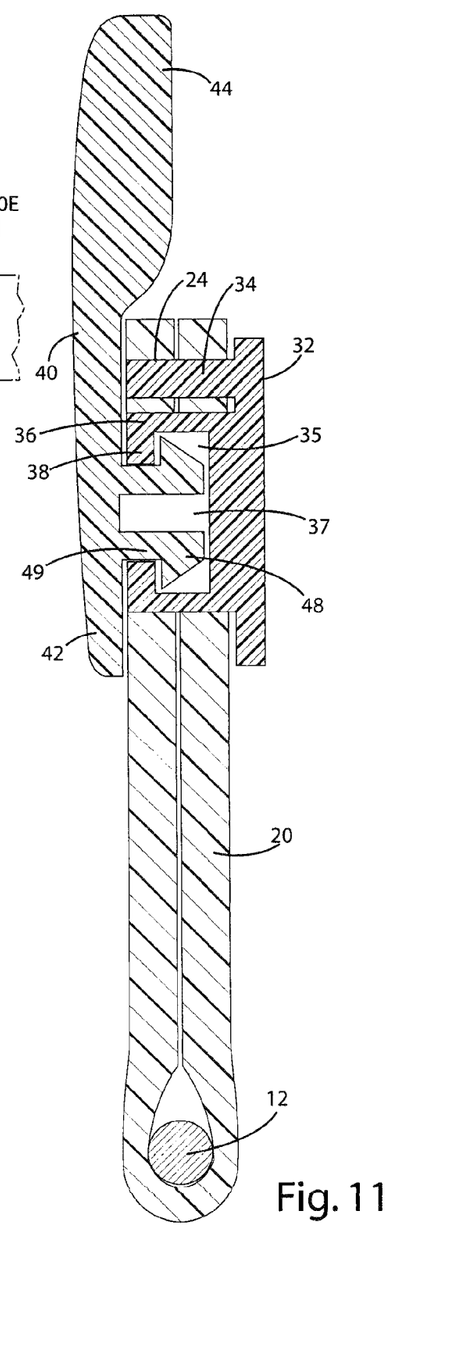
FIG. 11 is a cross-section of the foldable strap and clip taken along line 6-6 of FIG. 4.

The foldable strap portion 42 of the swivel tab 40 can engage the base 32 of the clip 30 in a variety of ways. For example, as shown in FIG. 8 the foldable strap portion 42 of the swivel tab 40 includes a button 46 with one or more fingers with ramped ends 48 and a neck 49. As shown in FIG. 11, the ramped ends 48 of the button 46 can snap fit into and interlock with the rail 38 on the raised ring 36 of the base 32 of the clip 30. The neck 49 and ramped ends 48 of the button 46 rotate on the rail 38 to provide a range of rotation for the swivel tab 40 relative to the base 32 of the clip 30, the foldable strap 20 and the frame 12. While the illustrated embodiment depicts the button 46 and rail 38 as snap-fit elements, it should be understood that any corresponding snap-fit elements can be used. Optionally, other screw fitted or mechanically connected elements can be used in place of, or in addition to, the snapfit elements.

The head strap portion 44 of the swivel tab 40 can be affixed to a head strap 50 of the protective eyewear 10 by joining the clip 30 to the head strap 50. The head strap 50 can extend around at least a portion of a player's head to position the eye protector members 18, 19, 21 over the player's eyes. The position of clip 30 relative to the player's head can allow the head strap 50, and in particular an end 50E, to rotate on the first side 14 and/or second side 16 of the frame 12 in a plane generally parallel to the player's temple, optionally about the swivel axis SA. Upon a desired amount of swiveling about the swivel axis SA, the head strap 50 can then be placed at any desired location on the player's head to accommodate the player's hair, hair accessories or for comfort, all while pulling the strap 20 to adequately pull the frame and hold it adjacent the wearer's face. A strap diverter 52 (discussed further below) can be positioned along the head strap 50, if desired, to divide the head strap 50 into first and second strap portions extending at an angle relative to one another and defining a space therebetween.

Figure 2:
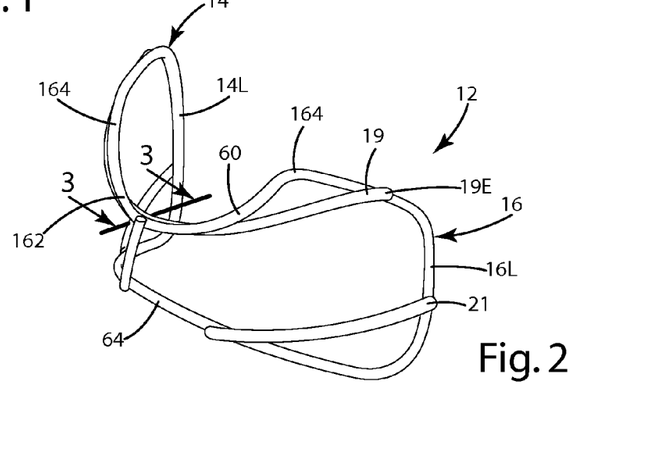
FIG. 2 is a perspective view of a frame of the protective eyewear.

The frame 12 can be formed in any shape that is suitable to support and retain the eye protector members 18, 19, 21 and to join with the foldable strap 20. As shown in FIG. 2, the frame 12 can include an upper member or portion 60 that spans between the first 14 and second 16 ends generally above a wearer's eyes or brows, and generally above upper eye protector member 19. That member 19 can span across a wearer's face, above the eyes, and can be substantially horizontal. The first 14 and second 16 ends can include first 14L and second 16L members that are optionally disposed at the outermost lateral extremities of the frame at the ends. These first 14L and second 16L members can be generally vertical, and can be joined with or an extension of the upper members 12 and/or 19, and/or lower member 64.

The upper member 60 can include sub-portions that are concave or convex relative to other elements of the frame 12. For example as shown in FIG. 2, a sub-portion 162 of the upper frame portion 60 can be slightly concave, indented or V-shaped at or near the center 162 of the upper member, which can rest on the player's forehead generally above the player's nose. The upper member 60 of the frame 12 also can include convex portions 164 laterally disposed relative to the center 162 on either side to accommodate at least a portion of the wearer's brow ridge. These convex portions can extend above the upper eye protector member 19 a preselected distance, and can join it at the ends 19E.

Figure 3:
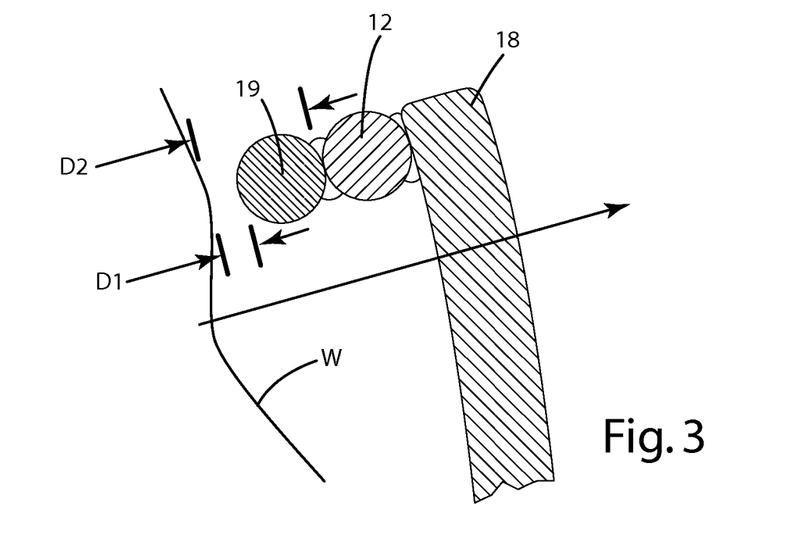
FIG. 3 is a cross-section of the frame of the protective eyewear taken along line 3-3 of FIG. 2.
Figure 4:
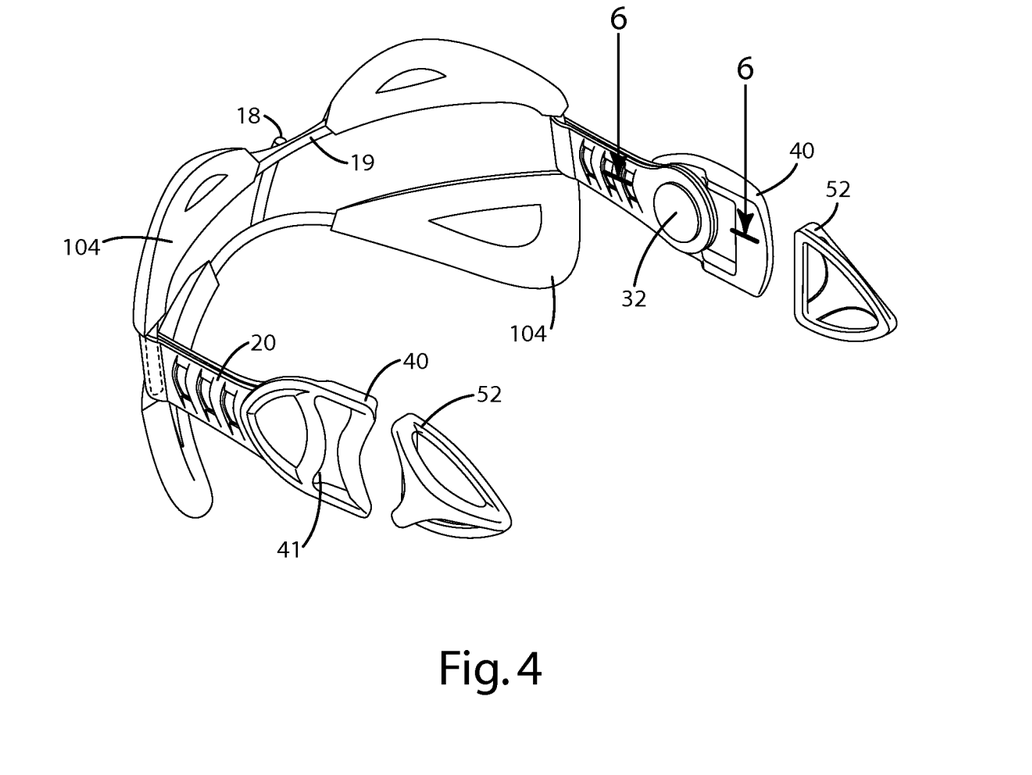
FIG. 4 is a rear perspective view of the protective eyewear.
Figure 5:
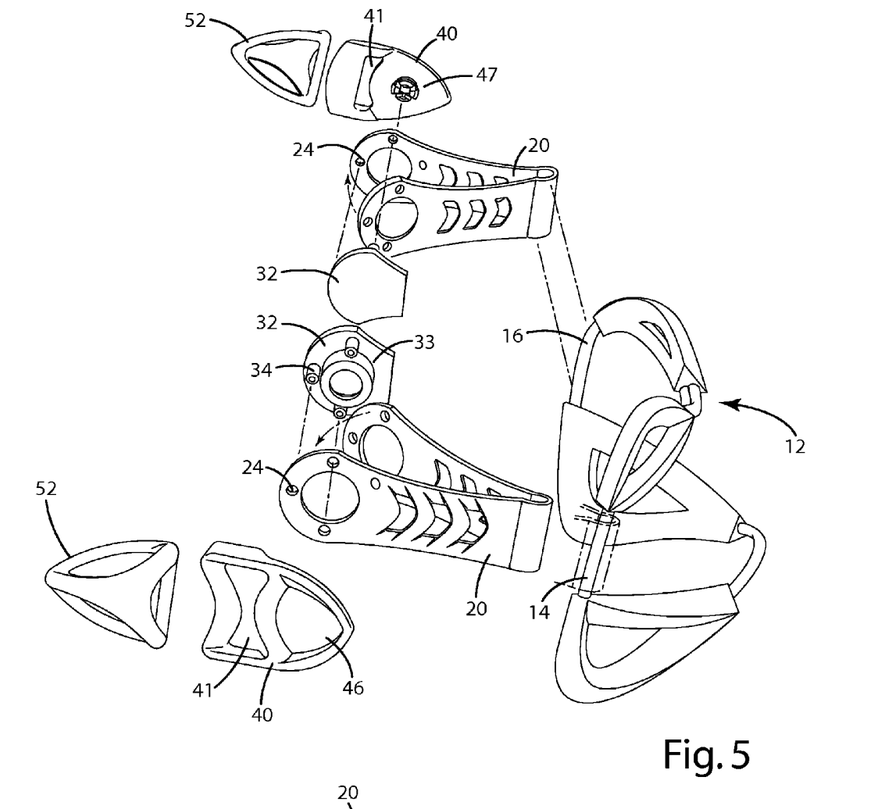
FIG. 5 is an exploded view of the protective eyewear.

As shown in FIGS. 2 and 5, the frame 12 can be curved in a concave orientation with respect to the face of the wearer, generally when looking down at the top of the eyewear. The upper eye protector member 19 can be stacked relative to and/or overlapping the upper frame portion 60. This stacking and/or overlapping of the upper frame portions 60 and upper eye protector member 19 can increase the structural rigidity of the frame 12, while decreasing the visual bulk of the eyewear 10 when viewing the eyewear in a front view. Generally, the protector members 18, 19 and frame member 60 are stacked, directly over one another in a direction D away from the wearer W as shown in FIG. 3. In this stacked configuration, the upper protector member 19 is a distance D1 from the wearer, and the frame 12 is a distance D2 from the wearer W. Distance D2 is greater than D1. Generally, in the stacked configuration, the upper protector member 19 is aligned substantially parallel to the frame member 60, for at least a distance over the wearer's nose, and optionally laterally outward over the wearer's brows. The members can be welded to one another, and optionally welded to the central, generally vertical protector member 18. This member 18 can be generally transverse and optionally perpendicular to both the frame member 60 and the protector member 19.

Optionally, as shown in FIG. 2, the upper eye protector member 19 can be secured to the frame member 60, generally in the center of the eyewear 10, over the bridge of the nose, with the member 19 close to the wearer there. However, the ends 19E of the member 19 can be secured to the frame member and particularly the convex portions 164, laterally outward from the wearer's nose in a different manner. For example, the ends 19E of the member can be distanced farther from the wearer than the frame member 60. Thus, the generally horizontal upper protector member 19 can undulate closer to and farther from the wearer relative to the member 60 across the wearer's face. Other members of the frame can undulate as well as desired.

Figure 1:
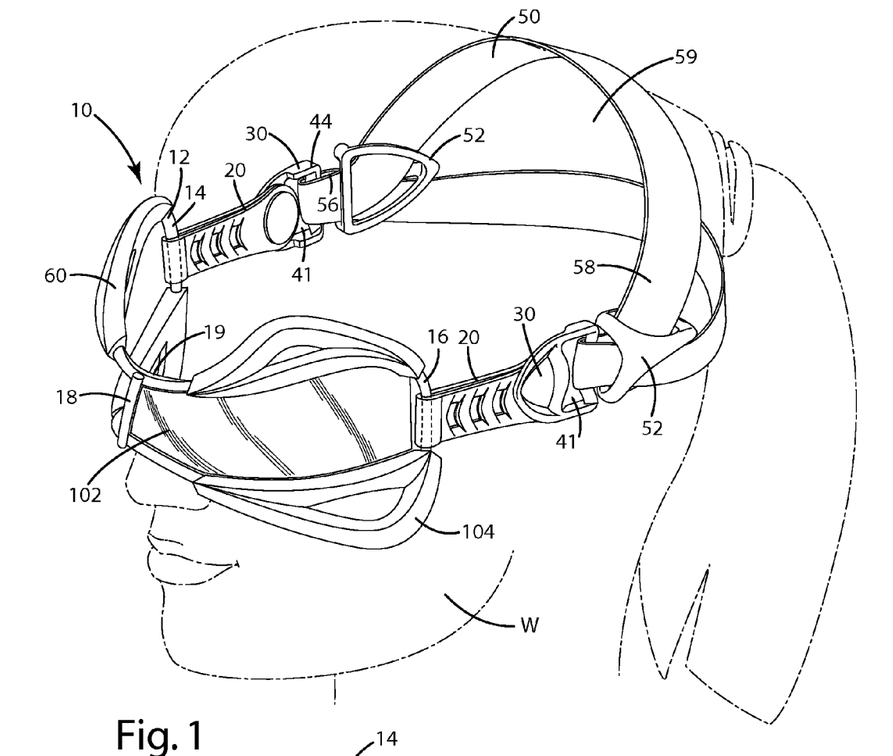
FIG. 1 is a front perspective view of a current embodiment of the protective eyewear donned by a wearer.

As shown in FIG. 1, the upper frame portion 60 angles down toward and terminates at the first and second ends 14 and 16, which generally correspond to the player's temples. The frame 12 also includes two lower eye protector members 21, which extend from the ends 14 and 16 or the members 14L and 16L, of the frame, respectively, on a downward angle toward the player's nose, generally across the wearer's cheeks. The lower eye protector members 21 can terminate at the respective sides of the player's face and generally can correspond to the player's cheeks. The central eye protector member 18 can be generally vertically disposed between the upper frame portion 60 and a lower frame portion 64. Thus, the frame 12 and the eye protector members 18, 19, 21 can form a cage positioned around the player's eyes so as not to obstruct the player's vision. Although not shown, the lower frame portion 64 and/or lower eye protector members 21, if desired, can extend over the player's nose and connect so that the lower portion of the frame is closed by those portions.

Optionally, the frame 12 and eye protector members 18, 19, 21 can be formed from any suitable material, including but not limited to, metal, rubber and polymers, such as thermoplastic elastomers, polyurethane, neoprene, polyethylene and can be rigid or flexible or partially flexible.

As shown in FIGS. 8 and 9, the swivel tab 40 portion of the clip 30 can engage the base 32 to assist in retaining the swivel tab 40 in the opening 22 of the foldable strap 20. In the illustrated embodiment, the swivel tab 40 includes an outer surface 45 and an inner surface 47 adapted to face an inner surface 33 of the base 32 (FIGS. 8 and 9).

The snap elements, the ramped ends 48 and neck 49 of button 46, can then slide along the rail 38, such that the swivel tab 40 is adapted to rotate with respect to the base 32. As shown in FIG. 9, multiple protrusions 34 can extend from the inner surface 33 of the base 32. The protrusions 34 are adapted to be inserted into openings 24 defined in the foldable strap 20. When the protrusions 34 are inserted into the apertures 24, the position of the base 32 is fixed with respect to the frame 12. Optionally, the protrusions and openings are designed so that a rotation limiter, if present, registers with the swivel tab 40 in a manner to provide the desired rotation limits.

With reference to FIGS. 9 and 11, the rail 38 can be selectively formed depending on the range and direction of motion desired for the swivel tab 40. The rail 38 can be generally formed as a circular ring that is spaced from and parallel with the inner surface 33 of the base 32. The snap elements in this case, the ramped ends 48 of the fingers and neck 49 of the button 46, are each configured to flex or bend a certain amount. When inserted into the generally circular rail 38, the ramped end 48 resiliently snaps under the rail 38, in the respective recesses between the rail 38 and the inner surface 33 of the base 32 (FIG. 11). The snap elements, that is the ramped ends 48 and neck 49 of the button 46, can then slide along the rail 38 within the recess 35 to allow the swivel tab 40 to rotate. Optionally, the rail 38 may include at least one rotation limiter to limit the rotational movement of the swivel tab 40.

Figure 10:
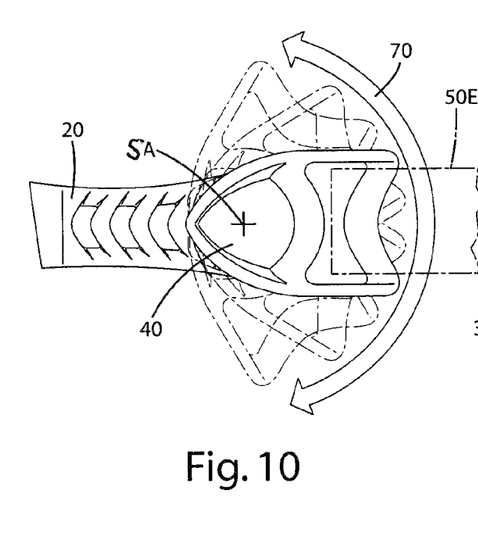
FIG. 10 is a detailed view of the foldable strap and clip.

Referring to FIG. 10, the range of rotation of the swivel tab 40 as shown by arrow 70 with respect to the base 32, folded strap 20 and frame 12, can be between 0° and 360°. If desired, rotational limiters or stops (not shown) can be positioned on the base 32 and/or the swivel tab 40 to limit the range of rotation of the swivel tab to, for example, 180° or 120° or any other range, as desired. To obtain a desired rotational range, the foldable strap 20 can be bent away from the swivel tab 40 to accommodate the rotation of the head strap portion 44 of the swivel tab 40 around or toward the frame 12.

The protective eyewear 10 can be retained over the player's face in any suitable manner. As illustrated in FIG. 1, the head strap 50 is used to retain the protective eyewear 10 over the player's face; however, the protective eyewear 10 alternatively can include a pair of end pieces that position over the player's ears, like a traditional pair of eyeglasses. The head strap 50 can be formed from an elastic material to allow the player to stretch the head strap 50 so that the protective eyewear 10 can be properly positioned on the player's head. After the player adjusts the frame 12 and the eye protector member 18 in the correct position, the elastic force of the strap will tighten the eyewear 10 against the player's face and head.

With reference to FIG. 1, the head strap 50 is threaded through the openings 41 in the respective swivel tab 40 portions of the clips 30, and the ends of the head strap 50 are connected together to form a closed loop. In this configuration, a portion of the head strap 50 is located adjacent the player's head, and a portion overlaps or overlays the strap, such that an inner surface 56 of the head strap 50 contacts and rests against an outer surface 58 of the head strap 50 when the strap is stretched over the player's head.

The protective eyewear 10 can include at least one strap diverter for directing the strap surfaces 56, 58 over specific areas of the player's head. For example, two strap diverters 52 can retain the strap surfaces 56, 58 together at two locations along the strap 50. As shown in FIG. 1, the diverters 52 retain the strap surface 56, 58 adjacent to one another in an area between the foldable strap 20 and the diverter 52. As the overlapping head strap 50 exits the diverters 52, the diverters 52 separate the strap surfaces 56, 58 of the overlapping head strap 50. As a result, a space or opening 59 is created between the strap portions respective to the surfaces 56, 58. Optionally, the opening 59 can be sized to accommodate a player's loose hair or ponytail as shown in FIG. 1. The opening 59 also allows the elastic force of the head strap 50 to be distributed more evenly across the back of the player's head.

The position of the diverters 52 along the strap 50 is adjustable, such that the size and the location of the opening 59 can be adjusted. For example, the size of the opening 59 could be tightened or widened to accommodate the player's ponytail or to adjust the distribution of elastic force from the head strap 50. Optionally, the opening 59 can be tightened to secure the head strap 50 about a lacrosse stick or other piece of equipment for storage or transportation when the protective eyewear 10 is not being worn. The diverters 52 can be adjusted by sliding the diverters 52 independently along the head strap 50 to the desired location. The diverters 52 can be formed in any suitable shape and size to divert and converge the strap portions to create the opening 59. The diverters 52 can be identical, such that only diverter 52 can be described in detail.

With reference to FIG. 2, the eye protector members 18, 19, 21, as the other components 14, 16, 60, 64 of the frame 12 can be formed in any configuration suitable to help protect the player's eyes from blows during play, while maintaining the player's line of sight. The frame 12 can provide spring action that can dissipate impact and shock more effectively than other types of eye protectors, such as goggles. To maintain an unobstructed central field of view for the player, in the illustrated embodiment, eye protector members 18, 19, 21 are arranged so that no member is directly in front of the player's eyes. However, the openings between the components of the frame 12 are arranged to be sufficiently close together to prevent objects such as lacrosse sticks or lacrosse balls from penetrating between the cage created by the components 14, 16, 18, 19, 21, 60, 64. Optionally, at least one lens 102 can be included between the members. Further optionally, although shown as a cage, the eye protector members 18, 19, 21 can be formed as a lens, for example a polycarbonate lens, joined with the frame.

The frame 12 can be formed from any suitable material, including metals, alloys, composite or synthetic materials. Optionally, one or more of the components 14, 16, 18, 19, 21, 60, 64 can be formed from mild spring steel wire, which can meet the ASTM standard for women's adult and youth lacrosse. The components can be weldable and formable, to allow the wire elements 86 to be resistance-welded or spot-welded to each other. Optionally, the components of the frame 12 can have a protective coating, such as rubber or a synthetic material, and can be finished to remove any sharp edges that could cut a player. The parts of the frame 12 can be joined with the frame 12 in any suitable manner.

The protective eyewear 10 can be formed to cover any desired portions of the face. For example, in addition to covering the player's eyes, the protective eyewear 10 of the illustrated embodiment covers the player's facial area around the eyes and a portion of the player's temples and nose.

As shown in FIG. 2, the protective eyewear 10 can include padded portions 104. The padded portions 104 can be adapted to provide a comfortable barrier between the player's face and the frame 12, such that the player's face substantially engages the padded portions 104 and not the remaining portion of the frame 12. The padded portions 104 can be selectively positioned on the frame 12 to engage desired portions of the player's facial area. For example, the padded portions 104 are positioned on the upper frame portion 60 and/or on the eye protector member 19. Additionally or alternatively, the padded portion 104 can be positioned on the lower frame and/or eye protector member 21. Optionally, the padded portions 104 can be removable from the frame 12, such that the player can selectively attach and remove the padded portions 104 from the frame 12 as desired.

The padded portions 104 can be formed from any suitable material, such as a material that will not cause skin irritation or undergo substantial physical changes as a result of contact with the face or skin. For example, the padded portions 104 can be formed from a low density foam material or a polymeric material. Optionally, the padded portions 104 can include a dual-density open or closed cell foam, for example, using a three pound density foam in contact with the face and a six pound density foam layer against the frame 12. The lower density layer can be more comfortable against the face, while the higher density foam can provide better impact protection.

As desired, the protective eyewear 10 can be customized to reflect the player's team name, logo, colors or other identifier. For example, the outer surface 45 of the swivel tab 40 can be adapted to include the identifier, which can be molded or printed thereon. Additionally, the various elements of the protective eyewear 10 can be molded or formed from materials in the player's team colors.

While the illustrated embodiment has been described in connection with the sport of women's lacrosse, it should be understood that the protective eyewear of the present invention is suitable for use by both male and female players of an essentially unlimited number of indoor and outdoor sports and other non-sport activities.

The above description is that of the current embodiment of the invention. Various alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention can be replaced by alternative elements that provide substantially similar functionality or otherwise provide adequate operation. This includes, for example, presently known alternative elements, such as those that might be currently known to one skilled in the art, and alternative elements that can be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "the," is not to be construed as limiting the element to the singular. Any reference to claim elements as "at least one of X, Y and Z" is meant to include any one of X, Y or Z individually, and any combination of X, Y and Z, for example, X, Y, Z; X, Y; X, Z; and Y, Z.

The embodiments of the invention in which an exclusive property or privilege is claimed are defined as follows:

1. A protective eyewear comprising:
    a frame, comprising:
        a first side including a first member and an opposing second side including a second member;
        a lower member extending below the first and second members;
        an upper member extending above the first and second members, the upper member extending between the first side and the second side, above the lower member, with at least one eye opening defined between, the upper member and the lower member,
    a strap including first and second opposing ends, the first end defining a first opening, the second end defining a second opening, the strap being folded over upon itself so that the first opening and the second opening are substantially aligned with one another, and so that at least one of the first member and the second member is disposed between the first and second opposing ends;

a clip including a base and a swivel portion rotatably engaged with one another, at least one of the base and the swivel portion being disposed in at least one of the first opening and the second opening defined by the strap, the swivel portion having a range of rotation relative to the base; and an elongated head strap attached to the swivel portion of the clip, the elongated head strap including an end joined with the swivel portion, the end being moveable within the range of rotation of the swivel portion.

2. The protective eyewear of claim 1 wherein the range of rotation is 360 degrees.

3. The protective eyewear of claim 2 wherein the range of rotation is 180 degrees.

4. The protective eyewear of claim 3 wherein the range of rotation is 120 degrees.

5. The protective eyewear of claim 1 wherein the strap includes a first inner surface and a second inner surface, wherein the first inner surface lays over and engages the second inner surface when the strap is folded over upon itself.

6. The protective eyewear of claim 5 wherein the strap includes a folding axis at which the strap is folded, wherein the first member is disposed adjacent the folding axis and trapped between the first inner surface and the second inner surface when the strap is folded over upon itself.

7. The protective eyewear of claim 6 wherein the folding axis is located in a center of the strap, about midway between the first and second opposing ends of the strap.

8. The protective eyewear of claim 1 wherein the strap folds over upon itself about a folding axis, wherein the strap includes a folding feature, wherein the first member is disposed adjacent the folding feature when the strap is folded over upon itself.

9. The protective eyewear of claim 8 wherein the strap defines a plurality of slots between the first and second openings.

10. A protective eyewear comprising:

a frame having a first side including a first member and an opposing second side including a second member;

a folded strap defining an opening at each of two opposing ends, the folded strap folded about and at least partially surrounding a portion of the frame with the openings at each end substantially aligned;

a clip having a base and a swivel portion rotatably engaging one another, at least one of the base and swivel portion being disposed at least partially through at least one of the openings of the folded strap, and a head strap attached to the swivel portion of the clip so that the head strap is moveable with the swivel portion whereby the head strap can be reoriented in a plurality of positions around a wearer's head.

11. The protective eyewear of claim 10 wherein the frame comprises an upper portion and a lower portion, at least one of the upper and lower portions joined with at least one of the first and second side members.

12. The protective eyewear of claim 10 wherein the frame includes an upper protective member and an upper member, wherein the upper protective member is in a stacked arrangement with the upper member as viewed from a front view when the eyewear is worn by a wearer.

13. The protective eyewear of claim 12 wherein the upper member is joined with a substantially vertical protective member located opposite the upper protective member.

14. The protective eyewear of claim 12 wherein the frame is constructed from a plurality of metal bars welded to one another.

15. The protective eyewear of claim 12 wherein the foldable strap includes a folding feature and a folding axis, wherein the foldable strap is folded at the folding axis.

16. The protective eyewear of claim 12 wherein the swivel portion is rotatable about a swivel axis, wherein the head strap includes a strap end, wherein the strap end is adapted to be swiveled to a plurality of positions about the swivel axis, but wherein the head strap exerts a tension on the foldable strap that retains the frame adjacent a wearer's face regardless of the position of the strap end.

17. A protective eyewear comprising:

a frame;

a strap folded about and entrapping a portion of the frame, the strap defining an opening;

a clip being disposed at least partially through the opening of the strap; and a head strap attached to the clip so that the head strap is moveable with the clip about a swivel axis whereby the head strap can be reoriented in a plurality of positions around a wearer's head.

18. The protective eyewear of claim 17 wherein the clip includes a swivel portion that is joined with an end of the head strap.

19. The protective eyewear of claim 17 wherein the strap includes a folding axis, wherein the folding axis is configured to be substantially vertical when the strap entraps the portion of the frame.

20. The protective eyewear of claim 17 wherein the strap defines another opening, wherein both openings of the strap are aligned with one another, wherein the clip is disposed through both openings defined by the strap.

* * * * *